United States Patent [19]
Baker et al.

[11] Patent Number: 5,579,778
[45] Date of Patent: Dec. 3, 1996

[54] METHOD AND APPARATUS FOR PRODUCING THERMODILUTION CARDIAC OUTPUT MEASUREMENTS UTILIZING A NEURAL NETWORK

[75] Inventors: Phillip D. Baker, Portland, Oreg.; Joseph Orr; Dwayne R. Westenskow, both of Salt Lake City, Utah; Royce W. Johnson, Ventura, Calif.

[73] Assignee: University of Utah Research Foundation, Salt Lake City, Utah

[21] Appl. No.: 294,938

[22] Filed: Aug. 23, 1994

Related U.S. Application Data

[63] Continuation-in-part of Ser. No. 119,451, Sep. 9, 1993, Pat. No. 5,339,818.

[51] Int. Cl.$^6$ ............................................. A61B 5/00
[52] U.S. Cl. ............................ 128/691; 128/713; 128/692
[58] Field of Search ..................................... 128/668, 713, 128/692, 691

[56] References Cited

U.S. PATENT DOCUMENTS

| | | |
|---|---|---|
| 3,726,269 | 4/1973 | Webster, Jr. . |
| 4,819,655 | 4/1989 | Webler . |
| 4,941,475 | 7/1990 | Williams et al. . |
| 5,092,343 | 3/1992 | Spitzer et al. . |
| 5,146,414 | 9/1992 | McKown et al. . |
| 5,261,411 | 11/1993 | Hughes . |
| 5,339,818 | 8/1994 | Baker et al. . |
| 5,390,679 | 2/1995 | Martin ..................................... 128/713 |

OTHER PUBLICATIONS

Tim Studt, Neural Networks: Computer Toolbox for the 90's.

*Primary Examiner*—Angela D. Sykes
*Assistant Examiner*—Robert L. Nasser, Jr.
*Attorney, Agent, or Firm*—Thorpe, North & Western

[57] ABSTRACT

A method and device for indirect, quantitative estimation of cardiac output utilizing invasive, indirect techniques. The method of practice includes (i) generating a sequence of signals which are quantitatively dependent upon cardiac output, (ii) transmitting and processing the signals within a computer system and associated neural network capable of generating a single output signal for the combined input signals, (iii) directly determining an actual value for the parameter concurrent with the invasive generation of signals of the previous steps, (iv) applying weighting factors within the neural network at interconnecting nodes to force the output signal of the neural network to match the known value of the parameter as determined invasively, (v) recording the input signals, weighting factors and known value as training data within memory of the computer, and (vi) repeating the previous steps to develop sufficient training data to enable the neural network to accurately estimate parameter value upon future receipt of on-line input signals. Procedures are also described for preclassification of signals and artifact rejection. Following training of the neural network, further direct measurement is unnecessary and the system is ready for diagnostic application and invasive estimation of parameter values.

13 Claims, 6 Drawing Sheets

METHOD AND APPARATUS FOR
PRODUCING THERMODILUTION CARDIAC
OUTPUT MEASUREMENTS UTILIZING A
NEURAL NETWORK

This is a continuation-in-part of application Ser. No. 08/119,451 filed on Sep. 9, 1993, now U.S. Pat. No. 5,339,818.

BACKGROUND OF THE INVENTION

1. Field of the Invention

The present invention utilizes a neural network to estimate cardiac output using thermal dilution. Specifically, an improved implementation of a standard catheter device combined with the nonlinear analyzing ability of a neural network provides unattended, semi-continuous cardiac output measurements over an extended period of time.

2. Prior Art

Hemodynamic monitoring of patients is a primary method of obtaining information for overall patient status, particularly during an operation or intensive care. Of the methods available for invasive measurement of the volume of blood pumped by the heart during a given time interval, thermal dilution remains the most common method of determining cardiac output. Popularity of the method is due in part because only a single venous catheter is required, blood samples are not needed, the thermal indicator is inexpensive, and it is a relatively fast technique.

Thermal dilution operates on the principle of conservation of energy and in determining cardiac output is referred to more specifically as thermodilution. Typically, a 5 to 10 ml bolus of cold injectate is inserted into the venous circulation of the right atrium through the lumen of a catheter. The bolus mixes with the blood and travels into the right ventricle of the heart, then passes by the thermistor located at the tip of the catheter placed in the pulmonary artery. Changes in blood temperature occur over time as the bolus is washed out of the heart, and result in an energy change in the blood flowing through the artery. Blood temperature is measured to create a thermal dilution curve from which cardiac output is derived.

The thermodilution method of measuring cardiac output is currently considered the accepted standard by physicians. However, there are many sources of error in the method, as well as problems inherent to the method itself that reduce effectiveness. For example, a typical source of error includes mishandling of injectate. Thermodilution is a function of injectate volume and temperature. Careful control of injectate administration is required to produce accurate readings, and readings can only be partially corrected for errors that do occur. Other errors are loss of indicator through the wall of the catheter, and thermal noise in the pulmonary artery. However, unlike injectate handling, correcting for thermal noise is much more difficult. These errors not only affect accuracy of cardiac output estimates, but also the repeatability of the measurement.

Despite widespread use, typical methods of thermodilution also suffer from being inconvenient and time consuming. Accurate measurements require careful set up of equipment, and close attention to injection intervals. The attending nurse or physician must also spend time waiting between injections, thus making cardiac monitoring expensive. In addition, volume loading of a patient from repeated injections of saline is hazardous when the patient suffers from congestive heart failure or renal dysfunction, thereby limiting continuous or ongoing application. The method is also not applicable for unattended patient monitoring because of the procedures involved in injecting the bolus. For these reasons, the method remains relegated to periodic spot checks, but is still used because of greater accuracy compared to noninvasive methods, and simplicity over other invasive techniques.

Several attempts have been made to improve on the method, but they too suffer significant drawbacks. For example, a heating element was introduced on a catheter that intermittently heats the blood flowing by it. However, because the amount of heat must remain low to avoid destruction of red-blood cells, the signal-to-noise ratio is high. To compensate, a number of measurements are averaged, resulting in a measurement of cardiac output that is 6 to 10 minutes old. In addition, the specialized catheter with a heat coil increases the method cost. Although the reading is semi-continuous, the infrequency of output makes this method inapplicable for many uses.

Other attempts include the injection of a room temperature bolus, or reduction of the bolus size. Although these variations on the method perhaps reduce the difficulty of handling injectate, they suffer from a low signal-to-noise ratio that makes repeatability of estimates difficult.

What is needed is a fresh approach to thermodilution estimates of cardiac output that can 1) compensate for a low signal-to-noise ratio, 2) increase applicability by reducing volume loading, 3) reduce errors caused by handling of bolus injectate or coolant as the injectate will now be referred to, 4) only require the introduction of a single catheter into the patient's heart, and 5) provide a semi-continuous output that can be used during operating procedures as well as intensive care monitoring that does not require constant supervision.

OBJECTS AND SUMMARY OF THE INVENTION

It is an object of the present invention to provide a method and apparatus for collecting and processing invasive thermodilution data for a more accurate estimation of cardiac output.

It is a further object of the present invention to provide a method and apparatus for estimating a variable physiological parameter such as cardiac output with greater accuracy than can be achieved using the current thermodilution method.

It is a further object of the present invention to provide a method and apparatus for estimating cardiac output utilizing a neural network as a system for processing input data and ultimately calculating the cardiac output.

It is yet another object of the present invention to provide a method and apparatus for generating a body of training data for use as part of a neural network to assist in estimation and determination of cardiac output derived from the generated data having a nonlinear relationship with the values monitored.

A still further object of the present invention is to provide a method and apparatus for determining cardiac output despite the occurrence of thermal noise and other signal corrupting influences.

Another object of the present invention is to provide a method and apparatus for unattended invasive thermodilution estimation of cardiac output.

Another object of the present invention is to provide a method and apparatus for continuous invasive thermodilution estimation of cardiac output of patients where volume loading would have been a limiting factor in use of the typical thermodilution technique.

Yet another object of the invention is to provide a method and apparatus for invasive thermodilution estimation of cardiac output when the total cardiac flow volume is low and the technique would normally be inapplicable.

These and other objects are realized in a method for direct and invasive measurement of thermodilution data. The method comprises the steps of (i) coupling a temperature sensor to the patient to monitor pulmonary artery blood temperature, (ii) taking measurements of blood temperature through said means, (iii) transmitting said signals to a neural network for processing, (iv) processing said input to calculate cardiac output based on the input weighting factors previously stored in the network, and (v) generating said weighting factors by retrieving previously stored training data.

Other objects and features of the present invention will be apparent to those skilled in the art based on the following detailed description, in combination with the drawings provided.

DESCRIPTION OF PREFERRED EMBODIMENT

Figure 1:
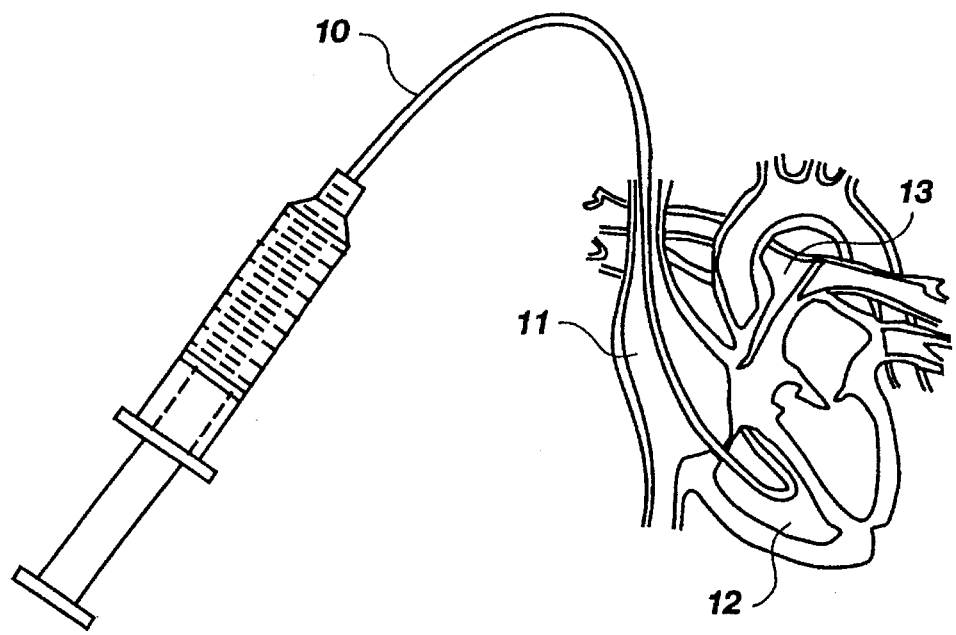
FIG. 1 is a graphic representation of a pulmonary artery catheter showing placement of the catheter.

FIG. 1 shows the positioning of the catheter 10 relative to the heart. In the current method of thermodilution, the catheter enters the right atrium 11, passes through to the right ventricle 12, and enters the pulmonary artery 13. In the conventional thermodilution method, the bolus would be injected through a lumen of the catheter into the right atrium. The fluid mixes with blood in the right ventricle, and then passes by the thermistor located at the distal end of the catheter.

Figure 2:
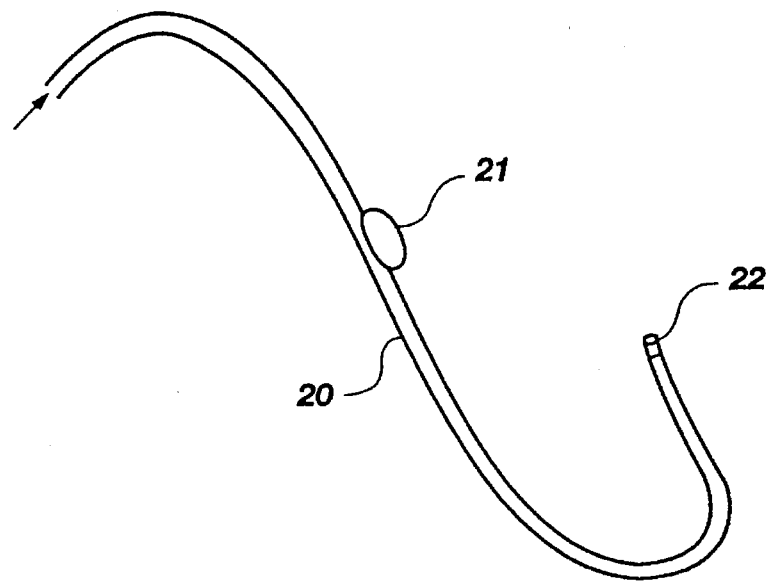
FIG. 2 is a representation of a catheter with the heat exchanger.

The present invention modifies the catheter in two ways. First, the lumen injection port in the right atrium is closed because the bolus is not injected into the blood of the heart. Second, a heat exchanger 21 is put in place of the injection port on the catheter 20. The heat exchanger 21, as illustrated in FIG. 2, is a thin but strong membrane that allows for heat exchange with blood in the vena cava. The chilled saline bolus is circulated between the membrane and the catheter 20. The blood returning to the heart is thus cooled as it passes by the membrane 21, continues through to the right ventricle, flows into the pulmonary artery, and passes by the thermistor 22 at the distal end of the catheter that measures the temperature depression of the venous blood mixture.

Figure 3:
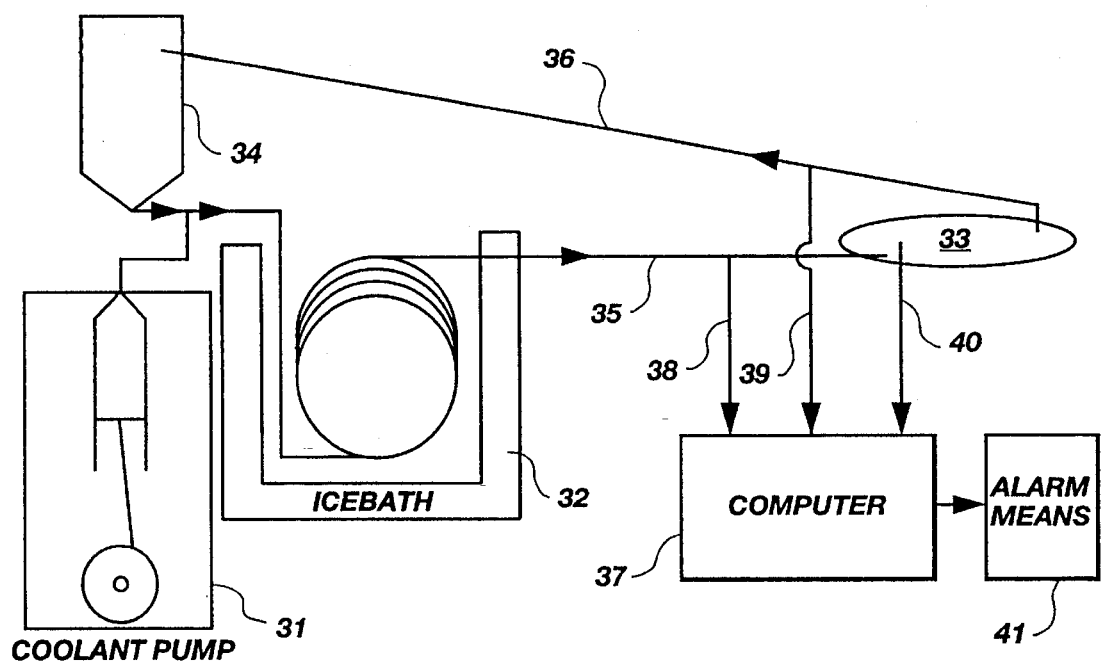
FIG. 3 is a block diagram illustrating the present invention, and the fluid flow path of the coolant.

FIG. 3 is a block diagram illustrating the external arrangement of components of the present invention comprising a fluid delivery system and a catheter. The diagram illustrates both the fluid flow path of the saline coolant, and the thermistor measurement data paths.

The advantages of the present invention are a far higher signal-to-noise ratio than is possible with a heating element system, as well as the inherent safety of not introducing a heating element into the patient. However, the invention does require additional equipment. As shown, there is a fluid delivery system comprised of a coolant circulating pump 31, the temperature modification reservoir 32 for chilling the coolant to allow unattended monitoring, and a storage reservoir 34 for warmed coolant that will be pumped into the temperature modification reservoir and chilled for a subsequent measurement.

The present invention requires an outlet path 36 for the saline returning from the heat exchange membrane 33, instead of being injected into the bloodstream. By returning the coolant through said outlet path 36, the fluid delivery system can function in a cycle by reusing the returned coolant. This cycle enables the present invention to operate unattended, producing semi-continuous cardiac output measurements.

The cycle can be traced from the temperature modification reservoir 32 where in the present invention the coolant is chilled. Said coolant is injected through an inlet flow tube 35 into the catheter heat exchanger 33. The chilled coolant displaces the warmed coolant already present in the catheter, pushing it through a return outlet path 36 to the fluid delivery system. This warmed coolant collects in a storage reservoir 34. The coolant is held in storage until a new measurement cycle begins, approximately every 32 seconds in this embodiment. A new measurement cycle begins when the pump 31 aspirates approximately 17 cc of warmed coolant from the storage reservoir 34, and injects said coolant into the temperature modification reservoir 32. Chilled coolant from this reservoir 32 again displaces warmed coolant in the catheter.

The chilled coolant injection process takes approximately 11 seconds. This interval is longer than the prior art because the present invention embodies a cyclical coolant path. This longer coolant path more significantly affects cardiac output calculations and requires careful measurement of thermal energy exchanged between blood and the coolant. This is because thermal energy is exchanged during the coolant injection/displacement process. Therefore, the temperature of chilled (inlet) coolant 38 entering the catheter and the warmed (outlet) coolant 39 leaving the catheter is measured over the entire 32 second cycle, including the time required to inject the coolant. These inlet and outlet coolant temperatures 38, 39 are then used to calculate the thermal energy exchanged between blood and coolant, referred to as "delivered energy."

The present invention also differs from the prior art technique in that it produces a more protracted thermal curve. This is a result of the longer injection period. The coolant must travel a longer path from the temperature modification reservoir 32 to the catheter heat exchange membrane 33, rather than from a syringe located near the entry of the catheter into the patient.

The diagram also indicates that the wiring 40 for the thermistor that measures pulmonary artery blood temperature travels a parallel path to the catheter. The thermistor is located at the distal end of the catheter, some distance from the heat exchange membrane 33 that is further back on the catheter length, as shown in FIG. 2.

Finally, the diagram illustrates that the computer 37 will generate a signal to alarm means 41 that notifies the monitoring personnel of failures within the system. There are four levels of notification that the system is capable of generating- alerts, alarms, errors and faults. Alerts will display an informative message, but not interrupt the cycle. Alarms beep repeatedly but also do not halt the cycle. Errors beep repeatedly with a pattern distinct from alarms, and will halt the cycle if it is running. Errors require a user to clear the state before operation can continue. Faults represent system failures which may indicate improper functioning of a system component. Faults beep repeatedly and require a user to clear the state. There is also an hierarchy of alarms, the order of priority being:

Faults>Errors>Alarms>Alerts

Higher priority problems will override lower priority, for example, if the system is malfunctioning and must be turned off.

Figure 4:
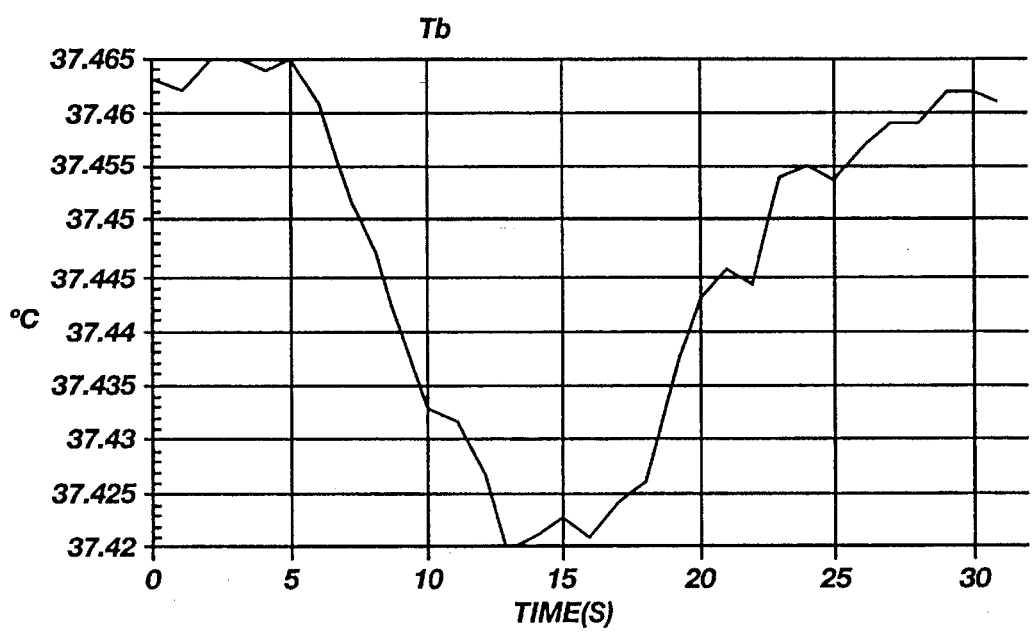
FIG. 4 is a graphical plot of a typical Constant Cardiac Output (CCO) thermal curve.

FIG. 4 is a graphical plot of a typical constant cardiac output thermal curve. The graph depicts blood temperature within the pulmonary artery versus time. As shown, the typical period of the measurement is 32 seconds, the period being the time the heart takes to flush the cooled venous blood from the heart and return to near the temperature before coolant was pushed into the catheter heat exchange membrane.

This waveform also illustrates another advantage of the present invention. Calculation of cardiac output using thermodilution normally requires use of the Stewart-Hamilton equation. This equation is based upon an energy balance method illustrated below:

$$CO = E_{input}/A * UN$$

where:
$E_{input}$=Energy delivered to the blood by heat exchange
CO=Cardiac Output
A=Area under thermal washout curve (integral of the change in blood temperature with time)
UN=Unit conversion factor which converts cc to liters, seconds to minutes, and corrects for differences in the specific heat and specific gravity of blood and 5% dextrose solution.

But this equation is not accurate under conditions of large end-diastolic volumes and/or low cardiac outputs because the waveform does not fully return to the baseline before the next 32-second cycle starts, as can be seen in FIG. 4. This fact and the need for noise tolerance are two reasons why the present invention is an innovative design. Utilizing a neural network gets around the failings of the Stewart-Hamilton equation allowing a wider range of invention application, as well as increased accuracy because of the ability of the neural network to view the waveform as a whole, not just some limited features of the curve, such as curve area.

Figure 5:
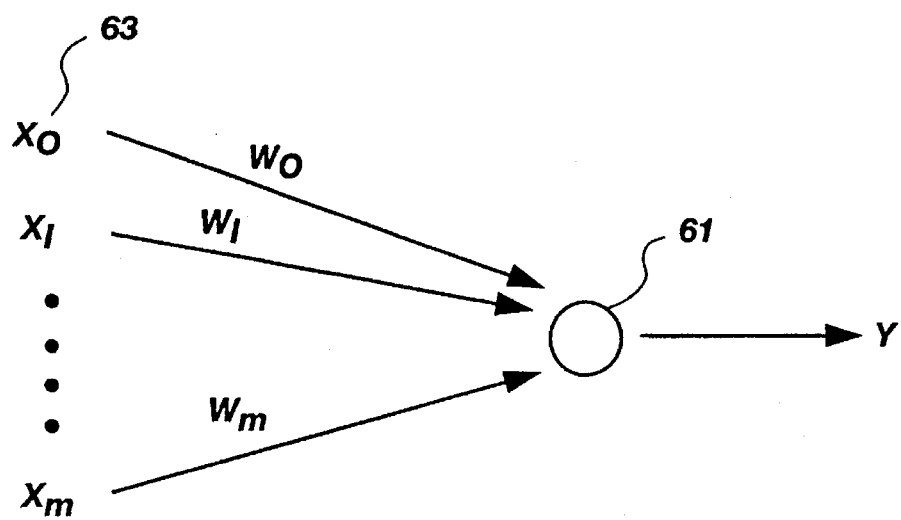
FIG. 5 is an illustration of the building block of neural networks, a single neuron.

As shown in FIG. 5, the basic building block of a neural network is the neuron 61. Each cell or neuron has an input side 63 that receives input data, shown here as $X_O$ through $X_N$, and an output side Y as illustrated. The input side 63 receives multiple signals that are weighted using weighting factors determined during training, while the output side Y is usually comprised of a single output signal. However, the present invention utilizes two neural networks, the first providing a single output as shown, the second providing a multiple output signal corresponding to the reliability of the estimated cardiac output that will be produced by the first neural network, as will be disclosed later.

Figure 6:
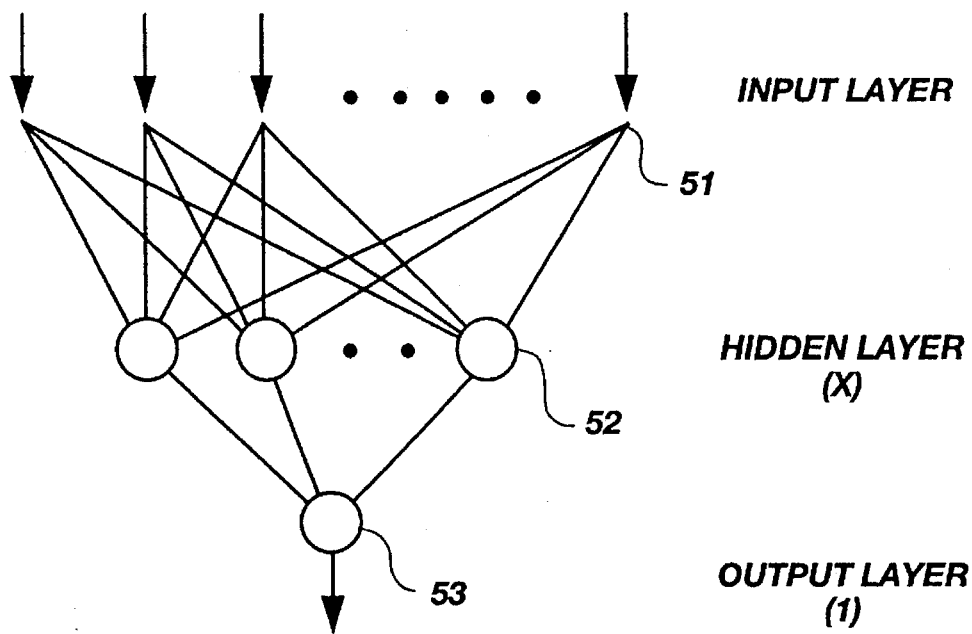
FIG. 6 is a graphic representation of an artificial neural network architecture used in the present invention.

FIG. 6 is a graphic representation of neural network structure. A neural network is a mathematical model similar to neural cells of a brain which are linked together to create a network that can be taught or trained to identify sets of inputs which appear to be similar to example input sets previously supplied to the network in a training situation. Once a neural network is trained, it provides a means of computing an appropriate output signal (such as cardiac output) when presented with a given input signal (such as a thermodilution waveform). Training data is used to modify the neural network weights as applied to various nodes making up the network until the network is optimized in a stochastic sense to provide the appropriate output for a given input. In the present invention, the form of neural network training is known as Backward Error Propagation and is well known to those skilled in the art.

The specific example of neural network structure of FIG. 6 consists of an Input Layer 51, a Hidden Layer 52, and a single Output Layer 53. The diagram should only be considered illustrative of the neural network concept. In practice, there can be many Hidden Layers 52 comprised of a varying number of nodes, as well as multiple output nodes in the Output Layer 53.

The present invention introduces an application of neural networks for calculation of cardiac output based on direct measurement of other parameters, i.e. blood temperature, by invasive means. Such estimations are feasible where a physiological event such as cardiac output can be monitored based on generation of a sequence of signals which are quantitatively dependent upon the variable physiological parameter.

The neural network can be trained to compute estimates of cardiac output from invasive measurements of blood temperature thermal curves produced by sampling pulmonary artery blood temperatures using the thermistor at the catheter tip, and measurement of coolant before and after injection into the heat exchange membrane. Because the network processes the entire thermodilution curve rather than trying to identify particular points such as maximum and minimum, the network is inherently less sensitive to noise than standard signal processing algorithms. The major strength of the neural network lies in its ability to provide nonlinear processing of the input curve, preventing the fluctuations of the curve produced by thermal noise from affecting the overall signal analysis.

A neural network may be specified in terms of its architecture. This includes the (i) number of nodes and the interconnection relationships between them, (ii) node characteristics such as input/output functions, and (iii) learning or training rules which define the method by which the node interconnections are adapted during training. The power of a neural network arises in part from the use of nonlinear functions to process node inputs and the use of parallel distributed processing wherein a given piece of information is not restricted to a single node but may appear as input to many nodes which may operate on the network inputs concurrently.

A continuously valued feed forward neural network was designed to process the thermal curves and produce the CCO estimate. Although reference is generally made throughout this disclosure to a single output layer, it is to be understood that multiple output nodes are implemented where separate and distinct output values are to be developed from the same set of output data. The CCO network shown in FIG. 9 is typical of the single output neural network, whereas the curve quality index CQI network also in FIG. 9 is a multiple output neural network.

Figure 7:
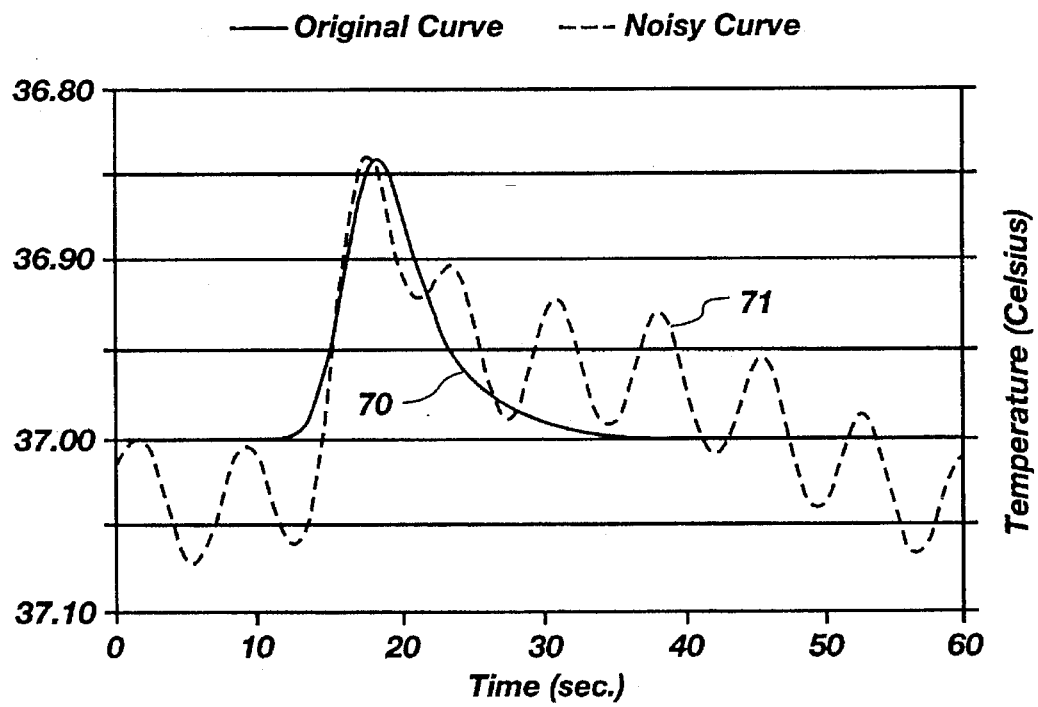
FIG. 7 is a graphical plot showing a typical CCO thermal curve, and a superimposed curve with noise.

FIG. 7 is a graphical plot of a thermodilution curve. The original curve 70 is a smooth line, and the noisy curve 71 is superimposed over the original curve. The plot illustrates the amount of noise that is present in a thermodilution curve. This result is not unexpected because of the scale of the measurements taken. Induced changes in pulmonary artery blood temperature are small, hence the difficulty in the method for obtaining accurate curves when thermal noise can be significant in comparison with actual blood temperature.

Figure 8:
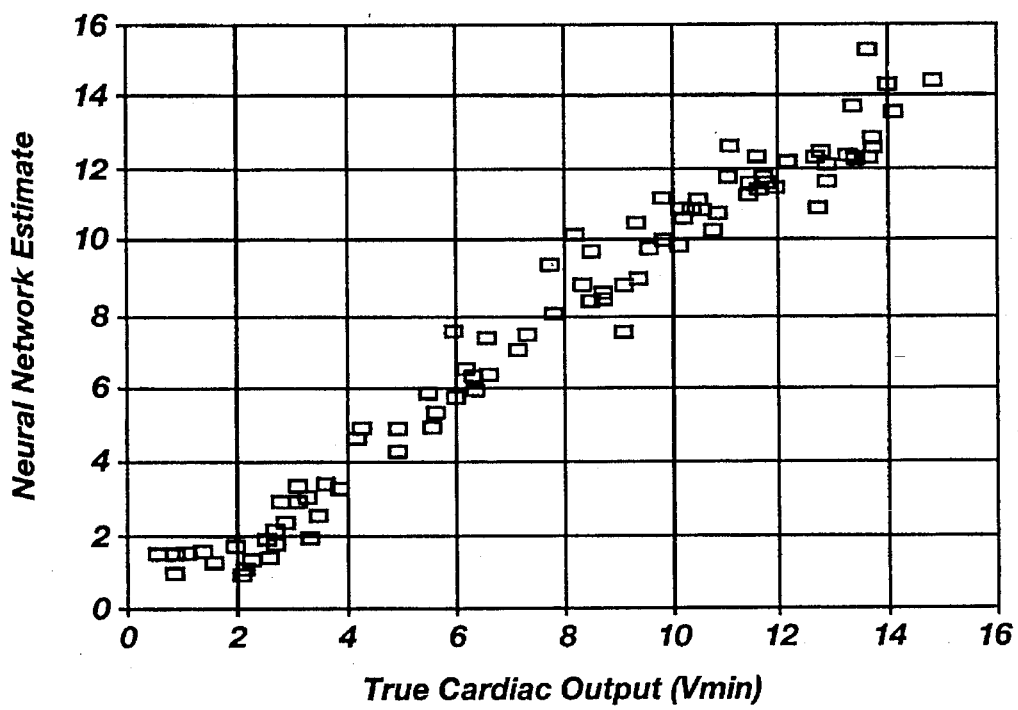
FIG. 8 is a graphical regression plot showing true cardiac output versus the neural network estimate.

FIG. 8 is a graphical regression plot illustrating results using simulation data of true cardiac output versus the neural network estimate. The standard error of the network results shown was 0.84, but in an animal trial, was reduced to 0.497.

Figure 9:
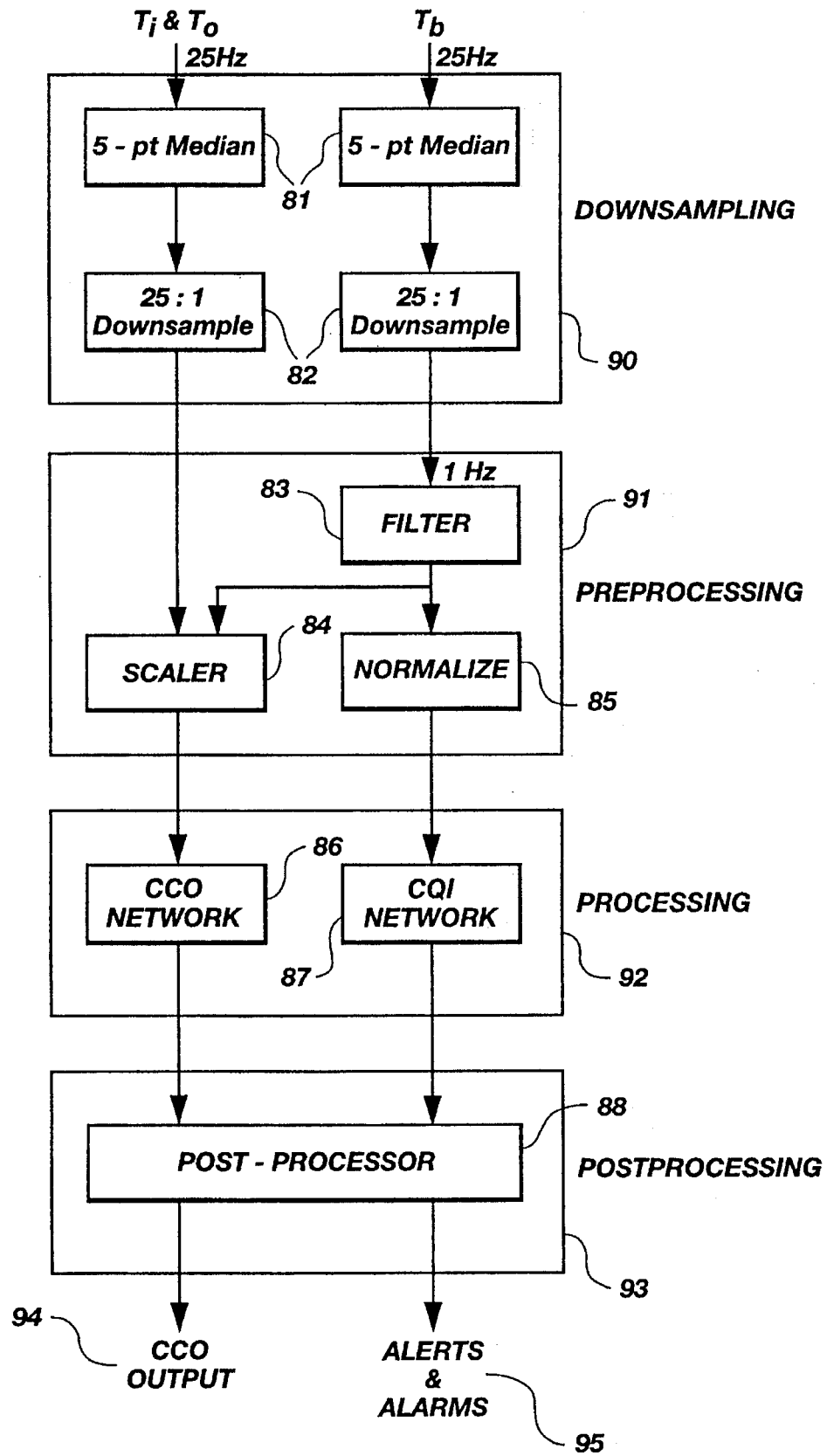
FIG. 9 is a flow chart representing the stages of CCO computation performed by the present invention, beginning with the sampling of the physiological parameter being monitored, the preprocessing, processing, and the final post-processing step resulting in the estimated CCO and any alerts and alarm conditions.

FIG. 9 is a flow chart of the stages of constant cardiac output (CCO) computation. The first stage in the computation is downsampling. The present invention samples data from three thermistors every 40 ms when a master clock interrupts the thermistor circuitry. This is a sampling rate of 25 Hz. When the circuit stabilizes after 16.6 ms, a thermistor produces a temperature reading of the patient's pulmonary artery blood temperature $T_b$, the outlet coolant temperature $T_O$, and the inlet coolant temperature $T_i$. The blood temperature reading is fed through a 5 point median filter 81, and then downsampled 82 to 1 Hz as preparation for input to the preprocessor. After the inlet and outlet coolant temperatures $T_i$ and $T_O$ are also downsampled 82 and filtered 81 to produce more accurate measurements, all measurements are then sen t to the computer for preprocessing 91.

The pulmonary artery blood temperature samples are contaminated with thermal noise, coolant injection artifact, and other types of unknown physiological noise such as instability of cardiac output. Thermal noise is reduced by passing the signal through a two pole low pass butterworth filter 83, and then backwards through the same filter to remove the phase shift induced by the first pass using the following difference equation:

1) Forward:

$$Y_n = gain*(X_n + 2*X_{n-1} + X_{n-2}) - b_1*Y_{n-1} - b_0*Y_{n-2}$$

(n=0 to 33)

2) Backward:

$$Z_n = gain*(Y_n + 2*Y_{n+1} + Y_{n+2}) - b_1*Z_{n+1} - b_0*Z_{n+2}$$

(n=31 to 0)

3) The smoothed curves are corrected for baseline drift:

$$Z_n = Z_n - slope*n$$

(n=0 to 31)

4) Finally, the smoothed and flattened curves are scaled by the delivered energy and referenced to the mean blood temperature.

$$W_n = 10000*[Z_n - average(Z_n)]/DE$$

(n=0 to 31)

where DE is the delivered energy to be discussed below.

After thermal noise has been filtered from $T_b$, $T_O$ and $T_i$, the temperature plots can be regarded as waveforms, representing one full cycle of pulmonary artery blood temperature change, and coolant temperature curves. The $T_b$ waveform is now processed using two different methods that are independent of each other. One sample of the waveform is scaled 84 by the energy delivered to the blood for use by the CCO network 86, and the other is normalized 85 for use by the CQI network 87.

First, scaling is accomplished by taking the 32 preprocessed $T_b$ points and executing an averaged subtraction with the following formula:

$$T_{bi} = T_{bi} - (\epsilon_{(j=1,32)} T_{bj}/32) \text{ for } i=1..32$$

The result is then scaled by the delivered energy with the following equation:

$$T_{bi} = 10000*T_{bi}/DE$$

The delivered energy is calculated using the following equation:

$$DE = p_s C_{ps} F_s \int_{t1}^{t2} (T4t1 - T3t1)dt - q_{m2s} - q_{sa}$$

where:
DE=Energy delivered to the blood by heat exchange
$p_s$=Density of saline
$C_{ps}$=Heat capacity of saline
$F_s$=Flow rate of saline through the catheter
T4t1, T3t1=Outlet and inlet saline temperatures entering or leaving the control volume of FIG. 10
$q_{m2s}$=Correction for transient heating or cooling of the catheter walls and fluids in the catheter lumens between injections.
$q_{sm}$=Correction for transient heating or cooling of the saline in the outlet and inlet catheter lumens.

The waveform is scaled by referencing to mean blood temperature in order to provide a baseline which is less impacted by noise. This scaled waveform is sent to the input nodes of the CCO neural network 86.

Figure 10:
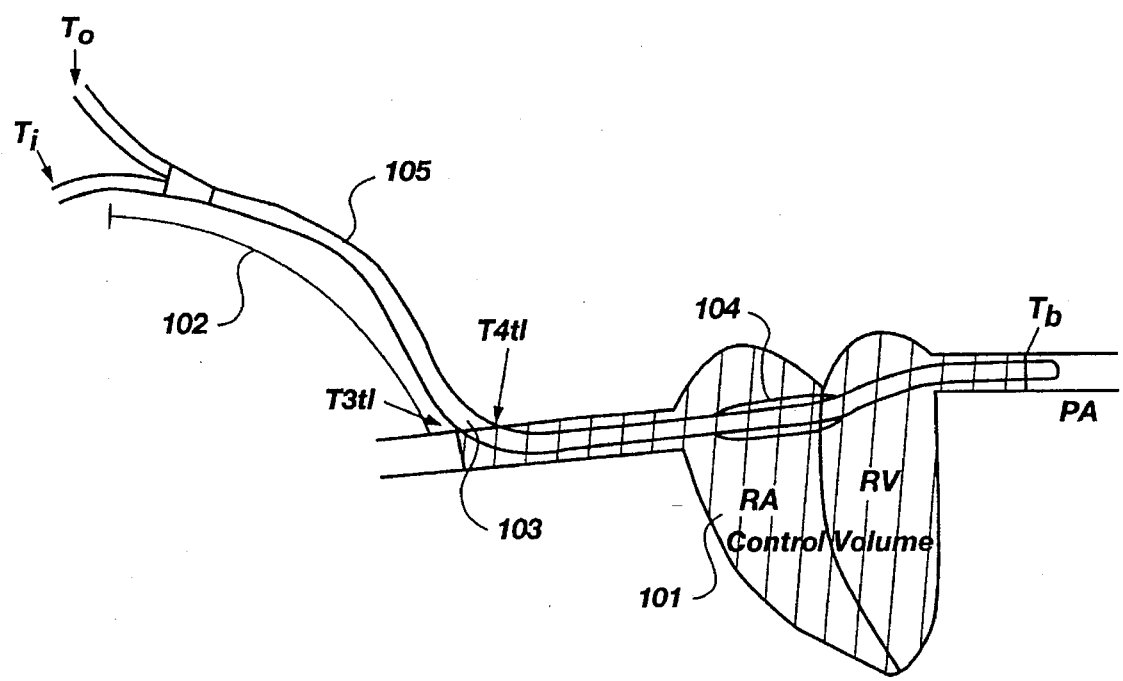
FIG. 10 is a graphic representation showing the relative relationship between a catheter, temperature measurement points, and a patient's heart.

The relationship between $T_i$ and $T_O$ and the temperature measurements T4t1 and T3t1 shown in the delivered energy equation above is illustrated in FIG. 10. There is measurable heat transfer between coolant and the environment outside the catheter along catheter length 102. To determine the energy transferred to the control volume 101, it is necessary to know inlet and outlet coolant temperatures at the point of entry 103 of the catheter into the bloodstream. Although the majority of heat transfer occurs through the heat exchange membrane 104, the entire catheter length within the bloodstream must be considered. Therefore, the control volume is defined as the catheter 105 and blood surrounding the catheter. T4t1 and T3t1 are also calculated by finding heat loss other than between the coolant and blood. This heat loss occurs in resistive networks defined as heat loss due to free convection between the saline and air, crossflow heat exchange between coolant in the inlet and outlet catheter lumens, and convection between coolant and tissue of the patient. Therefore, T4t1 and T3t1 are estimated based on $T_i$, $T_o$, ambient temperature, and the resistive networks.

Normalizing the waveform for CQI processing begins with the 32 filtered $T_b$ points being sorted for the maximum and minimum amplitudes, which are then subtracted for the difference, $DIF=T_{bmax}-T_{bmin}$. If the difference is less than 0.02 degrees Celsius, the CQI=0 and the CCO will be rejected. However, if the difference is greater, the waveform is normalized from 0 to 1, where $T_{bi}=(T_{bi}-T_{bmin})/DIF$ for (i=1 to 32). Normalizing allows waveforms that would otherwise be rejected to be kept because it is the shape of the waveform that is relevant, not the amplitude.

The filtering 83, normalizing 85, and scaling 84 of the waveform produced by the $T_b$ measurements constitutes the preprocessing phase 91 of the CCO computation. The next phase is the processing 92 of the normalized 85 and the scaled 84 waveforms through two separate neural networks 86 and 87. The scaled waveform is sent to the input nodes of the CCO neural network 86, and the normalized waveform is sent to the input nodes of the CQI neural network 87. The CCO neural network 86 produces a single output estimation of the cardiac output. The CQI neural network 86 is a method of quality control. The cardiac output 94 is only determined to be valid data if the thermal curve is of sufficient quality to be reliably free of noise as determined by the CQI neural network.

The CCO network 86 produces the constant cardiac output 94. The structure of the implemented neural network system includes an input layer, a bias node, twenty prototyping nodes in the clustering layer, 12 hidden nodes and a single output node. The specific architecture of the neural network is a radial basis function as known to those skilled in the art. The CCO network runs once per 32 second cycle, when acquisition and preprocessing of the signals is complete. The output of the CCO neural network is sent to the post-processor 93.

As mentioned previously, the curve quality index (CQI) neural network 87 has multiple outputs. Each filtered normalized thermal waveform is graded on a scale of 0 to 9. The neural network is trained to mimic experts who grade waveforms on this same scale. The CQI neural network 87 is implemented with 32 input nodes, a bias node, two layers of 16 hidden nodes each, and ten output nodes, where each output represents a level of quality. The specific architecture of the neural network is a multiple local expert system as known to those skilled in the art. A CQI value of 6 is the threshold to exclude noisy curves whose filtered output is considered unreliable. The CQI result is also sent to the postprocessor.

Finally, postprocessing 93 of both networks is accomplished with a three point Iridium filter 88. This particular filter will produce a running average of the previous two and the current CCO output that have CQI values greater than 6. When any of the last three waveform CQI values fall below 6, the CCO is the average of the other valid CCOs. If none of the last three CCO's were valid, an alert 95 is displayed.

The present invention thus comprises in general terms, the steps of (i) training a neural network to calculate cardiac output based on a given set of inputs, (ii) storing the generated neuron weighting factors produced from training in a computer, (iii) measuring changes in pulmonary artery blood temperature and the inlet and outlet coolant temperatures before and after coolant injection into the heat exchange membrane, (iv) transmitting these measured temperatures to the inputs of the neural network, (v) processing said inputs using the stored neural weighting factors to calculate cardiac output, and (vi) checking the validity of said cardiac output by evaluating the quality of the thermodilution waveform produced from the measurements of step iii, and discarding said cardiac output if quality of the waveform does not meet a predetermined criteria.

It will be apparent to those skilled in the art that the preceding disclosure is merely exemplary of the principles, methodology and apparatus, representing the subject invention. Accordingly, the specific embodiments and procedures are not to be considered as limiting with respect to the actual invention as defined by the following claims.

We claim:

1. A method for on-line calculation of cardiac output of a patient, said method comprising the steps of:

1.1) coupling at least one sensor to the patient, said sensor being responsive to register changes in blood temperature as part of a thermodilution procedure which includes bolus injection without volume loading of the patient;

1.2) activating the sensor to generate a sequence of on-line signals which register changes occurring in the blood temperature of a patient through direct indicator dilution signal measurements;

1.3) transmitting the on-line signals as input signals to a computer system, including input nodes of a neural network supported by the computer system, which neural network is capable of calculating a continuous output signal corresponding to a parameter value from the on-line, input signals;

1.4) preprocessing the input signals to produce a scaled waveform;

1.5) processing the input signals within the neural network to convert the sequence of input signals to an on-line output signal corresponding to a cardiac output value by applying fixed weighting factors to the input signals; and 1.6) retrieving said fixed weighting factors which were previously generated by applying a training algorithm with respect to previously collected training data comprising neural network input signals and corresponding known cardiac output values.

2. A method as defined in claim 1, further comprising the steps of:

2.1) selecting a plurality of sample signals from the sequence of signals for processing through a neural network which has been trained to associate such sample signals with a related value for the cardiac output; and 2.2) identifying at least one feature within the sample signals which can be processed through the neural network as a feature signal.

3. A method as defined in claim 2, wherein step 2.2 includes the step of identifying a blood temperature measurement as the feature which defines the feature signal, said method further including the step of developing a waveform based on the sampled signals generated in step 1.3, said waveform being represented by the pulmonary artery blood temperature measurements graphed over a time period comprising a single diagnostic measurement procedure.

4. A method as defined in claim 2 wherein step 2.2 comprises the more specific step of selecting the average of a plurality of blood temperature measurements as a single measurement procedure and processing the temperature signal of these sample signals to estimate the cardiac output without processing all pulmonary artery blood temperature measurements being generated.

5. A method as defined in claim 2, wherein step 2.2 includes the more specific steps as follows:

5.1) developing a waveform from the diagnostic measurement procedures comprising a predetermined number of sample signals, which number corresponds approximately to the number of input nodes existing in the cardiac output neural network;

5.2) storing in memory the sample signals; and 5.3) transmitting the stored sample signals of the waveform to respective input nodes of the cardiac output neural network.

6. A method as defined in claim 5, wherein step 5.1 comprises the more specific step of selecting the average of approximately 25 blood temperature measurements as a single measurement procedure and processing the temperature signal of these sample signals to apply on-line signals at the cardiac output neural network to estimate the cardiac output without processing all blood temperature measurements being generated.

7. A method as defined in claim 2 further comprising the more specific steps of:

7.1) generating a sequence of pulmonary artery blood temperature signals from a temperature sensing means within the patient's pulmonary artery;

7.2) identifying as a feature within the sampled pulmonary artery blood temperature signals to be a temperature value measured once every second over a time defined as the period of the waveform;

7.3) measuring and recording the pulmonary artery blood temperature values within the temperature sensing means to correspond to the signals of step 7.2);

7.4) transmitting the pulmonary artery blood temperature values to the computer system and input nodes of the neural network supported by the computer system for identification of the estimated cardiac output value based on comparison of on-line sample signals with a data base of training signals stored within computer memory; and 7.5) processing the on-line sample signals within the neural network to identify the estimated value of cardiac output associated with the sample signals.

8. A method as defined in claim 7, comprising the more specific step of measuring and recording pulmonary artery blood temperature values at predetermined time intervals over temperature ranges from approximately 23 to 43 degrees celsius.

9. A method as defined in claim 7, including the more specific step of selecting less than all generated signals of step 7.1 for transmittal to the input nodes of the neural network.

10. A method as defined in claim 9, comprising the more specific step of selecting a representative sampling of the generated temperature signals, said temperature signals to consist of approximately 32 points defining a single thermodilution curve waveform, where each point is the average of approximately 25 measurements, where the approximately 25 measurements occur within approximately a one second interval, thereby estimating the waveform developed by the signals transmitted to the input nodes of the neural network without requiring processing of all signals through all interactive nodes of the neural network to generate the desired output signal corresponding to the cardiac output.

11. A method for on-line calculation of a cardiac output of a patient, said method comprising the steps of:

11.1) coupling at least one sensor to the patient, said sensor being responsive to register changes in blood temperature with the patient as part of a thermodilution procedure which includes bolus injection without volume loading of the patient;

11.2) activating the sensor to generate a sequence of on-line signals which register changes in the blood temperature through direct indicator dilution signal measurements;

11.3) transmitting the on-line signals as input signals to a computer system, including input nodes of a neural network supported by the computer system, which neural network is capable of calculating a continuous output signal corresponding to the cardiac output from the on-line, input signals;

11.4) preprocessing the input signals to produce a scaled waveform;

11.5) processing the input signals within the neural network to convert the sequence of input signals to an on-line output signal corresponding to cardiac output value in accordance with the following substeps:

11.5a) processing the input signals within the neural network through at least one neural network layer having at least one node by applying fixed weighting factors to the input signals;

11.5b) retrieving said fixed weighting factors which were previously determined by applying a training algorithm with respect to previously collected training data comprising neural network input signals and corresponding known cardiac output values to generate said fixed weighting factors;

11.5c) for each input signal of each node within the neural network layer, calculating a product of the input signal and fixed weighting factor corresponding to each input signal and node combination;

11.5d) for each node within the neural network layer, summing the products of each input signal and fixed weighting factor combination calculated in the previous step 11.5c);

11.5e) for each node within the neural network layer, calculating a node output by applying an input/output function to the sum calculated in the previous step 11.5d);

11.5f) where the output of each node calculated in step 11.5e) represents the neural network output, displaying at least one node output as an estimated cardiac output value, or 11.5g) where the output of each node calculated in step 11.5e) represents the output of at least one hidden layer node, passing at least one output from outputs calculated in 11.5e) as input to any subsequent layer of nodes in the neural network.

12. A method as defined in claim 11, further comprising the steps of processing the output of the at least one hidden layer node from step 11.5g) by repeating steps 11.5c) through 11.5g) until the at least one node output defined in step 11.5f) representing the estimated physiological parameter has been displayed.

13. A method as defined in claim 11, wherein the step of 11.5b) retrieves previously determined weighting factors, comprising the more specific step of generating said previously determined weighting factors by:

13.4) determining an error between the known cardiac output value and the value generated by the neural network, and adjusting the weighting factors to modify the value of the output signal to match the known cardiac output value.

\* \* \* \* \*